United States Patent [19]

Phillips

[11] Patent Number: 5,125,416
[45] Date of Patent: Jun. 30, 1992

[54] GUIDEWIRE HOLDER

[75] Inventor: David A. Phillips, Boston, Mass.

[73] Assignee: University of Massachusetts Medical Center, Worcester, Mass.

[21] Appl. No.: 626,091

[22] Filed: Dec. 11, 1990

[51] Int. Cl.⁵ ............................................. A61B 5/00
[52] U.S. Cl. .................................. 128/772; 206/409
[58] Field of Search ................. 128/657, 772; 604/95, 604/164, 270; 206/305, 363, 364, 370, 569–572, 407, 409, 388

[56] References Cited

U.S. PATENT DOCUMENTS

| 3,301,393 | 1/1967 | Regan et al. | 206/409 |
| 4,351,333 | 9/1982 | Lazarus | 206/511 |
| 4,748,984 | 6/1988 | Patel | 128/658 |
| 4,925,448 | 5/1990 | Bazaral | 206/364 |

Primary Examiner—Max Hindenburg
Attorney, Agent, or Firm—Hamilton, Brook, Smith & Reynolds

[57] ABSTRACT

A guidewire holder is disclosed for storing guidewires in a storage fluid during surgical procedures. The guidewire holder comprises a spirally-wound tube which is configured to contain a storage fluid. The spirally-wound tube includes an upright entrance from which guidewires can protrude for selective retrieval and storage of a suitable guidewire during surgery. A spirally-wound portion extends from the upright entrance for receiving the guidewire from the upright entrance, thereby at least partially immersing the guidewire in the fluid.

18 Claims, 3 Drawing Sheets

GUIDEWIRE HOLDER

BACKGROUND OF THE INVENTION

Guidewires have enabled development of selective angiography, including coronary, cerebral, renal, hepatic, pancreatic and bowel angiography. Also, transcatheter embolization, pharmacologic vasoconstriction, and balloon angioplasty include use of such guidewires. Catheters inserted with guidewires have additionally been used for percutaneous drainage and removal of calculi from obstructed biliary and urinary systems. These procedures often require that the guidewire employed be of a precise diameter. However, several different guidewires can be required for a single procedure and differences in guidewire diameters generally can only be detected quickly by tactile comparison.

Open trays which are filled with a fluid, such as a heparin solution, are typically employed to immerse guidewires in preparation for their use. Guidewires are often inadvertently contaminated during a procedure due to lack of proper storage and must be discarded. Waste of guidewires, therefore, results when a guidewire of the same diameter is required twice during a single operation. In addition, guidewires are typically only loosely assembled in trays, often causing confusion and loss of time during selection of a suitable guidewire. Fluids can also be spilled easily from open trays. Further, a relatively large area of space is usually required for open trays, thereby reducing the mobility of physicians and nurses.

Therefore, a need exists for a new apparatus for storing and retrieving guidewires during cardiovascular (CV) or other interventional procedures which overcomes or minimizes the aforementioned problems.

SUMMARY OF THE INVENTION

This invention relates to a guidewire holder for storage and retrieval of guidewires.

A guidewire holder for storage and retrieval of a guidewire includes a continuous spirally-wound tube which is configured for containing a storage fluid. The spirally-wound tube has an upright entrance for receiving a guidewire and a spirally-wound portion extending from the upright entrance. The upright entrance is disposed substantially vertically and defines an upright entrance orifice which is disposed at a level relative to the spirally-wound portion sufficient to contain the storage fluid within the spirally-wound tube in an amount sufficient to at least partially immerse the guidewire in the storage fluid, thereby storing the guidewire.

This invention has many advantages. In general, the guidewire holder of the present invention substantially reduces the space typically required for storage of guidewires during cardiovascular procedures and interventional procedures such as urological and gastroenterological interventions. Further, guidewires can protrude from the guidewire holder for convenient access. The guidewire holder also stores guidewires closely together, thereby potentially reducing the time required to choose an appropriate guidewire. Fluid within which the guidewires are immersed is also less likely to be spilled from the guidewire holder than from an open tray.

DETAILED DESCRIPTION OF THE DRAWINGS

DETAILED DESCRIPTION OF THE INVENTION

The features and other details of the apparatus of the invention will now be more particularly described with reference to the accompanying drawings and pointed out in the claims. It will be understood that the particular embodiments of the invention are shown by way of illustration and not as limitations of the invention. The principal features of this invention can be employed in various embodiments without departing from the scope of the invention.

Figure 1:
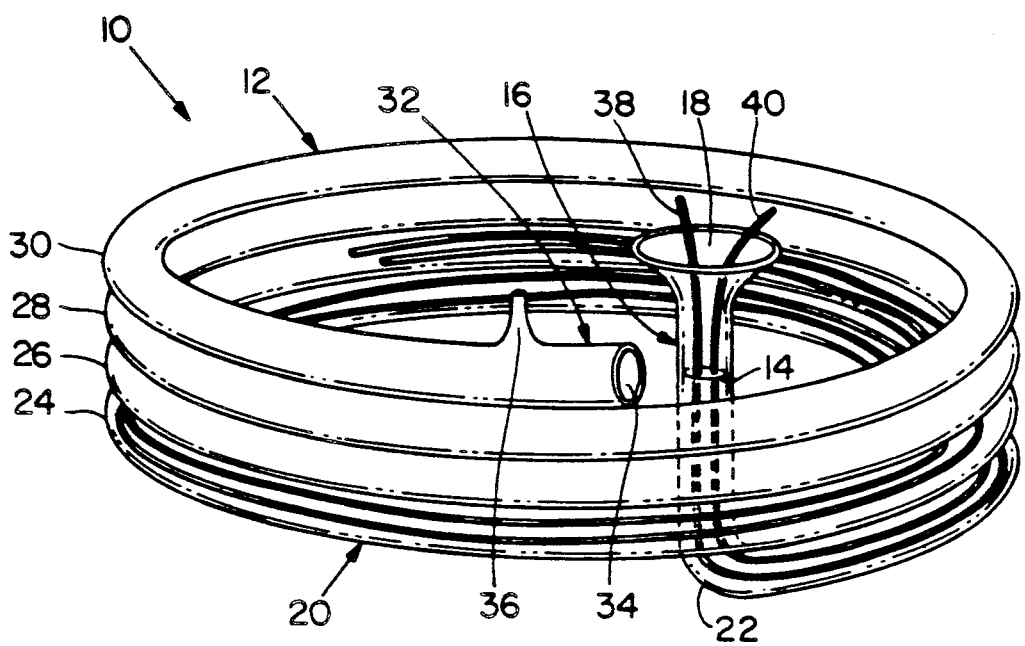
FIG. 1 is a perspective view of one embodiment of the guidewire holder of the invention wherein a lowermost spiral loop of a spirally-wound portion of a spirally-wound tube extends from an upright entrance of the spirally-wound tube and wherein the guidewire holder contains a storage fluid in which guidewires are partially immersed.

In one embodiment of the present invention, guidewire holder 10, illustrated in FIG. 1, comprises a spirally-wound tube 12 configured for containing storage fluid 14. Spirally-wound tube 12 is formed of a suitable material. In one embodiment, spirally-wound tube 12 is substantially rigid. Suitable rigid materials include those which are resistant to chipping or flaking by contact with guidewires and which are suitable for containing storage fluid 14 for storage of guidewires during cardiovascular and interventional procedures. Examples of suitable rigid materials include polymers such as Teflon ® polytetrafluoroethylene, glass, etc. In a preferred embodiment, guidewire holder 10 is formed of glass and is transparent for facilitating inspection of contents within guidewire holder 10.

Spirally-wound tube 12 includes upright entrance 16 which is disposed substantially vertically and defines upright entrance orifice 18. Upright entrance 16 is generally cylindrical and can be flared at upright entrance orifice 18. Upright entrance 16 can have an internal diameter in the range of between about one inch and about three inches. Upright entrance orifice 18 can have a diameter in the range of between about one and one-half inches and about three and one-half inches. In a preferred embodiment, upright entrance 16 has an internal diameter of about three inches and upright entrance orifice 18 has a diameter of about three and one-half inches.

A spirally-wound portion 20 of spirally-wound tube 12 extends from upright entrance 16. Spirally-wound portion 20 can include elbow 22 which is located where upright entrance 16 meets spirally-wound portion 20. Elbow 22 is contoured for gradual direction of objects contained within guidewire holder 10 from upright entrance 16 to spirally-wound portion 20.

Spirally-wound portion 20 can include a plurality of spiral loops. In one embodiment, spirally-wound portion 20 includes spiral loops 24,26,28,30. Spiral loops 24,26,28,30 are oriented substantially horizontally and are stacked substantially vertically. Spiral loops 24,26,28,30 are generally tubular. In a preferred embodiment, spiral loops 24,26,28,30 have a radius of curvature in a range of between about five and one-quarter inches and about six inches and have an internal diameter in the range of between about four and one-half inches and about five and one-quarter inches.

End portion 32 extends from spirally-wound portion 20 at uppermost spiral loop 30. Spirally-wound portion 20 provides fluid communication between upright entrance 16 and end portion 32. End portion 32 can define an end portion orifice 34 which is elevated above the storage fluid contained by spirally-wound tube 12. In a preferred embodiment, end portion 32 has an internal diameter which is about equal to the internal diameter of spirally-wound portion 20. The diameter of end portion orifice 34 is about equal to the internal diameter of end portion 32.

Guidewire holder 10 can include a flush port 36 which extends laterally from end portion 32. Flush port 36 extends from end portion 32 to a point above the storage fluid contained by spirally-wound tube 12. Flush port 36 can be dimensioned and configured for attachment of tubing, not shown, to thereby enable flushing of guidewire holder 10 with a suitable flushing fluid when quidewire holder 10 is not in use. An example of a suitable flushing fluid is a saline solution.

Guidewires 38,40 are disposed within guidewire holder 10 during storage. It is to be understood, however, that guidewire holder 10 is dimensioned and configured for storage of a sufficient number of guidewires to provide a suitable selection and quantity of guidewires during cardiovascular and interventional procedures. Guidewires 38,40 extend within upright entrance 16 and spirally-wound portion 20. Guidewires 38,40 can protrude from upright entrance 16 through upright entrance orifice 18 for tactile comparison and selection of a guidewire.

Guidewires 38,40 suitable for use with guidewire holder 10 include guidewires which are sufficiently flexible for storage and retrieval from guidewire holder 10. Particularly suitable guidewires are angiographic guidewires, such as are used by interventional radiologists or cardiologists for percutaneous catheterization. Examples of suitable angiographic guidewires include guidewires having a diameter in the range of between 0.014 and 0.038 inches which are commercially available from Cook, Inc. These guidewires include a fine, round cross-sectional wire of steel which is tightly coiled on a central core of safety wire formed of steel. The guidewires have a smooth outer coat formed of Teflon ® polytetrafluoroethylene.

Figure 2:
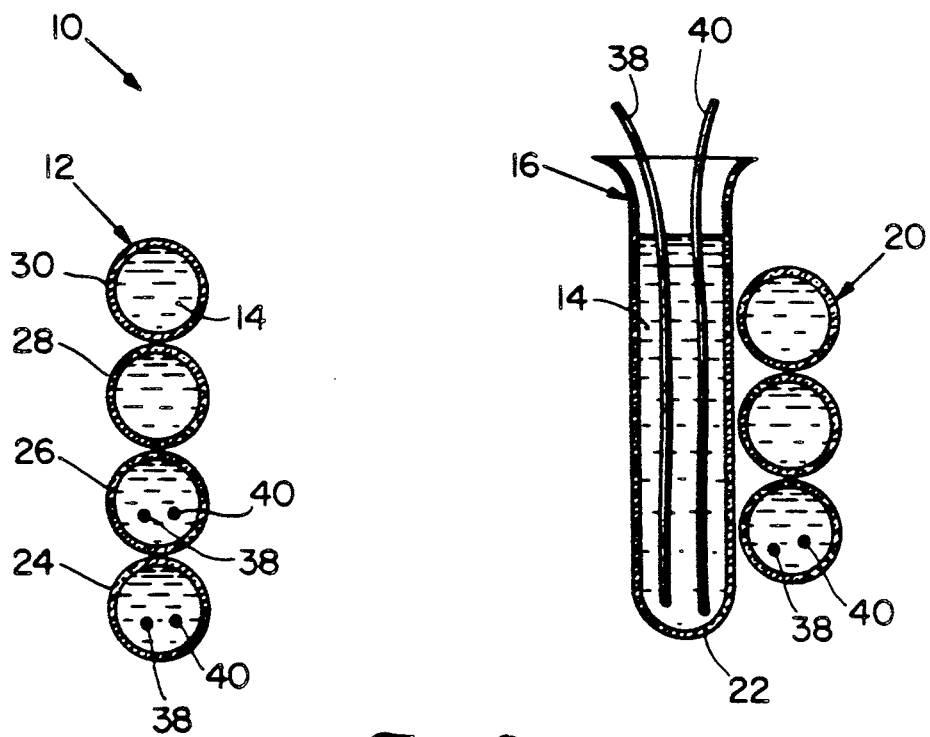
FIG. 2 is a sectional view of the embodiment shown in FIG. 1 wherein the guidewire holder contains a storage fluid in which guidewires are partially immersed.

As can be seen in FIG. 2, upright entrance orifice 18 is disposed at a level, relative to spirally-wound portion, which is sufficient to contain storage fluid 14 within the spirally-wound tube 12. Storage fluid 14 is suitable for storage of guidewires 38,40 before and during cardiovascular and other interventional procedures. An example of a suitable fluid for use with the present invention is a heparinized saline solution. An example of a suitable concentration of heparin is four units of heparin per ml of normal saline. Storage fluid 14 is contained within guidewire holder in an amount sufficient to at least partially immerse guidewires 38,40 in storage fluid 14, thereby storing guidewires 38,40.

When employed during a cardiovascular or other interventional procedure, guidewires 38,40 can be selectively removed from guidewire holder 10 by manually grasping either of guidewires 38,40. For example, guidewire 38 is grasped where guidewire 38 protrudes from guidewire holder 10 through upright entrance orifice 18. Alternatively, guidewires 38,40 can be completely immersed in storage fluid 14. When guidewires 38,40 are completely immersed, the selected guidewire 38 can be grasped either manually or by some other suitable means, such as forceps, not shown. Guidewire 38 is then withdrawn from guidewire holder 10 by pulling guidewire 38 where it has been grasped.

Following use, guidewire 38 can be returned to guidewire holder 10 by manually reintroducing guidewire 38 through upright entrance orifice 18 and into upright entrance 16. Referring again to FIG. 1, guidewire 38 is passed through upright entrance 16 and is gradually directed by elbow 22 into spirally-wound portion 20. Guidewire 38 is thereby at least partially reimmersed in storage fluid 14 for storage and subsequent retrieval.

Figure 3:
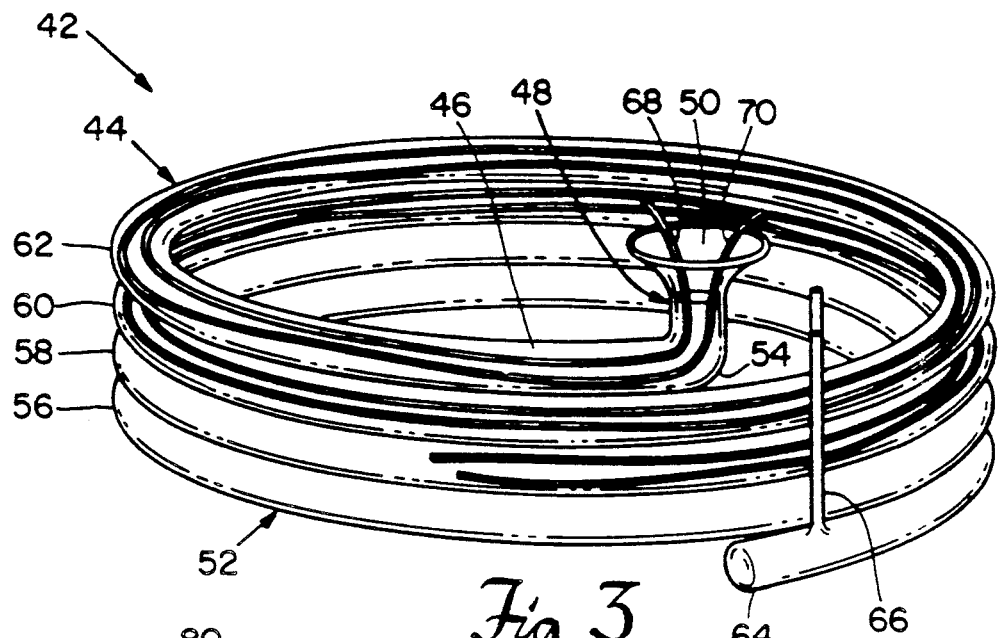
FIG. 3 is a perspective view of a second embodiment of the guidewire holder of the invention wherein an uppermost spiral loop of a spirally-wound portion of a spirally-wound tube extends from an upright entrance of the spirally-wound tube and wherein the guidewire holder contains a storage fluid in which guidewires are partially immersed.

In another embodiment of the present invention, illustrated in FIG. 3, guidewire holder 42 comprises spirally-wound tube 44. Spirally wound tube 44 is configured to contain storage fluid 46. Spirally-wound tube 44 includes upright entrance 48 which defines upright entrance orifice 50. Upright entrance orifice 50 is disposed at a level relative to spirally-wound portion 52 sufficient to contain storage fluid 46 within spirally-wound tube 44.

Spirally-wound portion 52 of spirally-wound tube 44 extends from upright entrance 48. In a preferred embodiment, spirally-wound portion 52 includes elbow 54 where upright entrance 48 meets spirally-wound portion 52. Elbow 54 is contoured for gradual direction of objects within spirally-wound tube 44 from upright entrance 48 into spirally-wound portion 52. Spirally-wound portion 52 also includes spiral loops 56,58,60,62. Spiral loops 56,58,60,62 are oriented substantially horizontally and are stacked substantially vertically. Upright entrance 48 extends substantially vertically from uppermost spiral loop 62 of spirally-wound portion 52 at elbow 54.

End portion 64 of spirally-wound tube 44 extends from lowermost spiral loop 56 and is sealed. Spirally-wound portion 52 provides fluid communication between upright entrance 48 and end portion 64. Flush port 66 extends substantially vertically from end portion 64 to a point elevated above uppermost spiral loop 60 for containing storage fluid 46 within spirally-wound tube 44. Flush port 66 is dimensioned and configured for attachment of tubing, not shown, to thereby enable flushing of guidewire holder 42 with a suitable flushing fluid.

Storage fluid 46 is contained by spirally-wound tube 44. Guidewires 68,70 are at least partially immersed in storage fluid 46. Partial immersion of guidewires 68,70 in storage fluid 46 by guidewire holder 42 thereby stores guidewires 68,70. Guidewires 68,70 can protrude from spirally-wound tube 44 through upright entrance orifice 50. Guidewires 68,70 can be manually grasped where they protrude through upright entrance orifice 50 for selective retrieval of guidewires 68,70 from guidewire holder 42.

Figure 4:
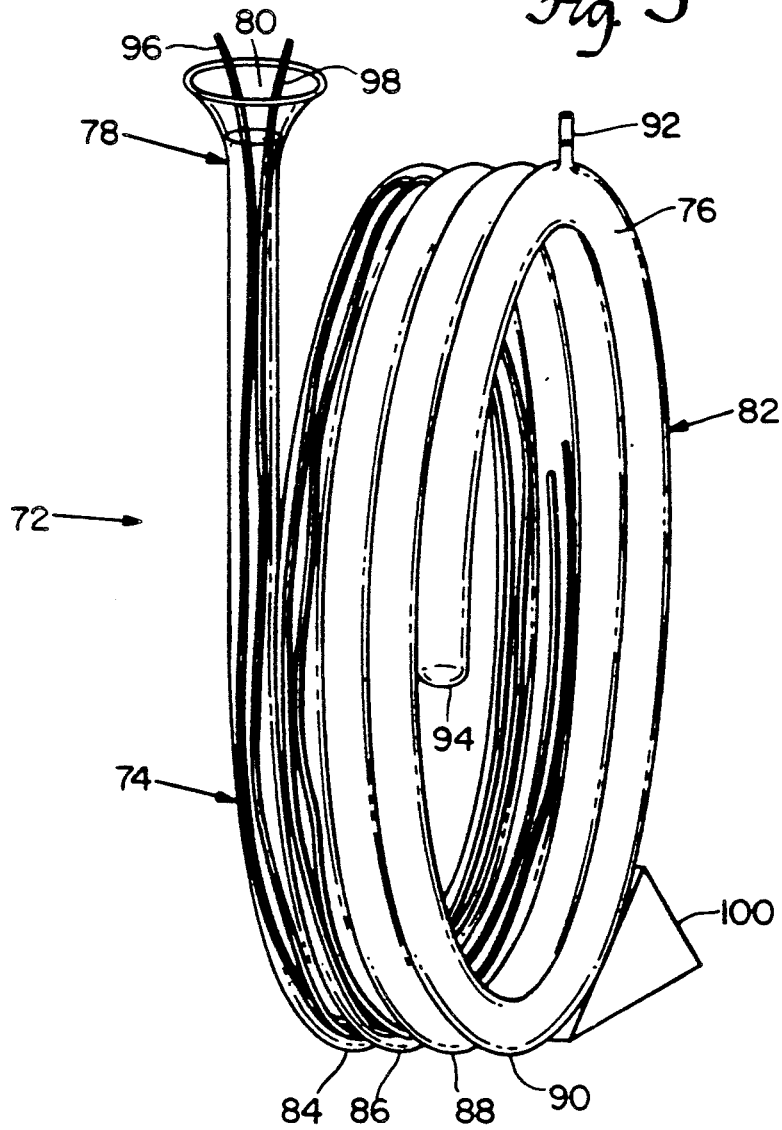
FIG. 4 is a perspective view of a third embodiment of the guidewire holder of the invention wherein spiral loops of a spirally-wound portion of a spirally-wound tube are oriented substantially vertically and wherein the guidewire holder contains a storage fluid in which guidewires are partially immersed.

In still another embodiment of the present invention, illustrated in FIG. 4, guidewire holder 72 comprises spirally-wound tube 74, which is configured to contain storage fluid 76. Spirally-wound tube 74 includes upright entrance 78 defining upright entrance orifice 80. Spirally-wound portion 82 extends from upright entrance 78 and includes spiral loops 84,86,88,90. Spiral loops 84,86,88,90 are oriented substantially vertically. A major axis of upright entrance 78 extends substantially vertically from spiral loop 84 and is coaxial to a line tangent to spiral loop 84 where upright entrance 78 meets spirally-wound portion 82. Flush port 92 extends vertically from spiral loop 90 to a point elevated above storage fluid 76. Storage fluid 76, such as a suitable heparin solution, is contained by spirally-wound tube 74. End portion 94 extends from spirally-wound portion 82. End portion 94 can be sealed for containing storage fluid 76 within spirally-wound tube 74. Guidewires 96,98 are at least partially immersed in storage fluid 76 because upright entrance orifice 80 is disposed at a level relative to spirally-wound portion 82 sufficient to contain storage fluid 76 within spirally-wound tube 74. Guidewires 96,98 extend from upright entrance 78 through upright entrance orifice 80. Guidewires 96,98 can be grasped where they protrude through upright entrance orifice 80 for selective retrieval of guidewires 96,98 from guidewire holder 72. Guidewire holder 72 can be stabilized by a suitable support 100.

Figure 5:
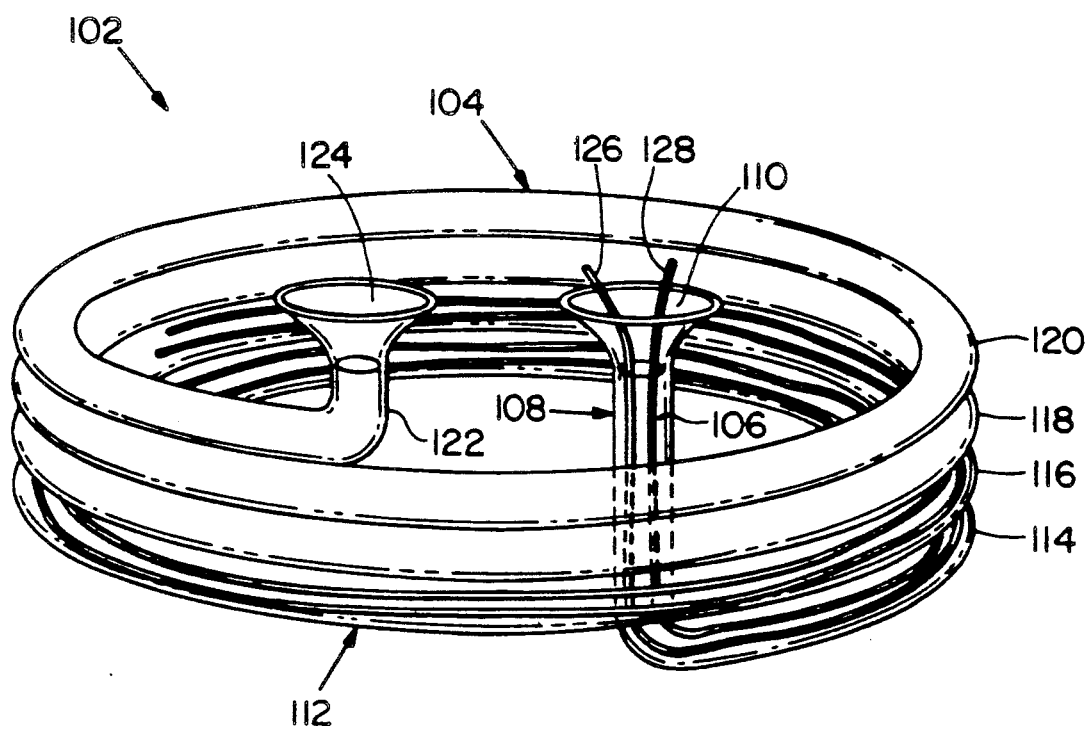
FIG. 5 is a perspective view of a fourth embodiment of the guidewire holder of the invention wherein an upright end portion extends from an uppermost spiral loop.

In another illustration of the present invention, shown in FIG. 5, guidewire holder 102 comprises spirally-wound tube 104, which is configured to contain storage fluid 106. Spirally-wound tube 104 includes upright entrance 108 defining entrance orifice 110. Upright entrance 108 can be flared at upright entrance orifice 110. Spirally wound portion 112 extends from upright entrance 108 and includes spiral loops 114, 116, 118, 120. Spiral loops 114, 116, 118, 120 are oriented substantially horizontally. A major axis of upright entrance 108 extends substantially vertically from spiral loop 114 where upright entrance 108 meets spirally-wound portion 112. Upright end portion 122 extends vertically from spiral loop 120 to a point elevated above storage fluid 106. Upright end portion 122 defines end portion orifice 124 and can be flared at end portion orifice 124. Preferably, end portion orifice 124 is level with entrance orifice 110 when guideline holder contains storage fluid 106. Guidewires 126, 128 are at least partially immersed in storage fluid 106 within spirally-wound tube 104 because entrance orifice 110 and end portion orifice 124 are disposed at a level relative to spirally-wound portion 112 sufficient to contain storage fluid 104 with spirally-wound tube 104. Guidewires 126, 128 extend from upright entrance 108 through entrance orifice 110. Guidewires 126, 128 can be grouped where they protrude through entrance orifice 110 for selective retrieval guidewires 126, 128 from guidewire holder 102.

The guidewire holder of the present invention is also suitable for storage and retrieval of catheters. Also, the apparatus of the present invention is suitable for storage and retrieval of wires for non-surgical uses, such as storage of plumber's "snaking" devices for flushing clogged water pipes and for storing cables.

Equivalents

Those skilled in the art will recognize or be able to ascertain using no more than routine experimentation, many equivalents to the specific embodiments of the invention described specifically herein. Such equivalents are intended to be encompassed in the scope of the following claims.

I claim:

1. A guidewire holder for storage and retrieval of a guidewire, comprising: a continuous spirally-wound tube configured for containing a storage fluid and having an upright entrance for receiving a guidewire and a spirally-wound portion extending from the upright entrance, the upright entrance being disposed substantially vertically and defining an upright entrance orifice which is disposed at a level relative to the spirally-wound portion sufficient to contain the storage fluid within the spirally-wound tube in an amount sufficient to at least partially immerse the guidewire in the storage fluid, whereby delivery of the guidewire through the upright entrance and into the spirally-wound portion at least partially immerses the guidewire in the storage fluid and stores the guidewire in the guidewire holder.

2. A guidewire holder of claim 1 wherein the spirally-wound tube is substantially rigid.

3. A guidewire holder of claim 2 wherein the spirally-wound portion includes a plurality of spiral loops.

4. A guidewire holder of claim 3 wherein the spiral loops are oriented substantially horizontally and are stacked substantially vertically.

5. A guidewire holder of claim 4 wherein the upright entrance extends from a lowermost spiral loop of the spiral portion.

6. A guidewire holder of claim 5 wherein the upright entrance is flared at the upright entrance orifice.

7. A guidewire holder of claim 6 wherein the continuous spirally-wound tube further includes an end portion which extends from the spirally-wound portion, whereby the spirally-wound portion provides fluid communication between the upright entrance and the end portion.

8. A guidewire holder of claim 7 whrein the end portion extends substantially vertically from the spirally-wound portion to form an upright end portion.

9. A guidewire holder of claim 8 wherein the upright end portion defines an upright end portion orifice.

10. A guidewire holder of claim 7 further including a flush port at the end portion for delivering a flushing fluid to the spirally-wound tube to thereby flush the guidewire holder.

11. A guidewire holder of claim 10 wherein the flush port extends laterally from the end portion to a point above the storage fluid contained by the spirally-wound tube.

12. A guidewire holder of claim 11 wherein the spirally-wound portion further includes an elbow where the spirally-wound portion extends from the upright entrance, the elbow being contoured for directing guidewires from the upright entrance into the spiral portion.

13. A guidewire holder of claim 12 wherein the end portion defines an upright flared end portion orifice providing fluid communication between the spiral portion and the atmosphere.

14. A guidewire holder of claim 13 wherein the spirally-wound tube is substantially transparent.

15. A guidewire holder of claim 14 wherein the spirally-wound tube is formed of a material selected from the group including glass and a polymer.

16. A guidewire holder for storage and retrieval of a guidewire, comprising: a rigid continuous spirally-wound tube configured for containing a storage fluid, having a spirally-wound portion which includes a plurality of spiral loops oriented substantially horizontally and vertically stacked, and an upright entrance extending from a lowermost spiral loop, the upright entrance being disposed substantially vertically and defining an upright entrance orifice for receiving a guidewire, the upright entrance orifice being disposed at a level which is sufficient to contain the storage fluid within the spirally-wound tube in an amount sufficient to at least partially immerse the guidewire in the storage fluid, whereby delivery of the guidewire through the upright entrance and into the spirally-wound portion at least partially immerses the guidewire in the storage fluid and stores the guidewire in the guidewire holder.

17. A guidewire holder for storage and retrieval of a guidewire, comprising: a rigid continuous spirally-wound tube configured for containing a storage fluid, having a spiral portion which includes a plurality of spiral loops oriented substantially horizontally and vertically stacked, and an upright entrance extending from an uppermost spiral loop, the upright entrance being disposed substantially vertically and defining an upright entrance orifice for receiving a guidewire, the upright entrance orifice being disposed at a level which is sufficient to contain the storage fluid within the spirally-wound tube in an amount sufficient to at least partially immerse the guidewire in the storage fluid, whereby delivery of the guidewire through the upright entrance and into the spirally-wound portion at least partially immerses the guidewire in the storage fluid and stores the guidewire in the guidewire holder.

18. A guidewire holder for storage and retrieval of a guidewire, comprising: a rigid continuous spirally-wound tube configured for containing a storage fluid, having a spirally-wound portion which includes a plurality of spiral loops oriented substantially vertically, and an upright entrance extending from the spirally-wound portion, the upright entrance being disposed substantially vertically and defining an upright entrance orifice for receiving a guidewire, the upright entrance orifice being disposed at a level which is sufficient to contain the storage fluid within the spirally-wound tube in an amount sufficient to at least partially immerse the guidewire in the storage fluid, whereby delivery of the guidewire through the upright entrance and into the spirally-wound portion at least partially immerses the guidewire in the storage fluid and stores the guidewire in the guidewire holder.

* * * * *